(12) United States Patent
Gonzalez et al.

(10) Patent No.: US 6,929,637 B2
(45) Date of Patent: Aug. 16, 2005

(54) DEVICE AND METHOD FOR INTRA-BRONCHIAL PROVISION OF A THERAPEUTIC AGENT

(75) Inventors: Hugo X. Gonzalez, Woodinville, WA (US); Steven Chase Springmeyer, Bellevue, WA (US); Richard O. Shea, Kenmore, WA (US); John H. Wang, Sammamish, WA (US); Lauri J. DeVore, Seattle, WA (US)

(73) Assignee: Spiration, Inc., Redmond, WA (US)

( * ) Notice: Subject to any disclaimer, the term of this patent is extended or adjusted under 35 U.S.C. 154(b) by 99 days.

(21) Appl. No.: 10/317,667

(22) Filed: Dec. 11, 2002

(65) Prior Publication Data

US 2003/0158515 A1 Aug. 21, 2003

Related U.S. Application Data

(63) Continuation-in-part of application No. 10/081,712, filed on Feb. 21, 2002, and a continuation-in-part of application No. 10/178,073, filed on Jun. 21, 2002.

(51) Int. Cl.$^7$ ................................................. A61K 9/22
(52) U.S. Cl. ..................................... 604/890.1; 604/11
(58) Field of Search .......................... 604/30–34, 96.01, 604/246, 247, 10–18, 890.1, 891.1; 606/108, 200, 213, 217, 119; 623/1.24, 1.26, 23.68, 1.25, 23.7, 2.26, 2.1; 600/16, 37; 607/2; 601/153

(56) References Cited

U.S. PATENT DOCUMENTS

| | | | |
|---|---|---|---|
| 2,981,254 A | 4/1961 | Vanderbilt | |
| 3,540,431 A | 11/1970 | Modin-Uddin | |
| 3,657,744 A | 4/1972 | Ersek | |
| 3,788,327 A | 1/1974 | Donowitz et al. | |
| 3,874,388 A | 4/1975 | King et al. | |
| 4,014,318 A | 3/1977 | Dockum et al. | |
| 4,086,665 A | 5/1978 | Poirier | |

(Continued)

FOREIGN PATENT DOCUMENTS

| | | |
|---|---|---|
| EP | 1 151 729 | 11/2001 |
| EP | 1157663 | 11/2001 |
| GB | 2 324 729 | 11/1998 |
| RU | 2140211 | 10/1999 |
| SU | 852321 | 7/1981 |

(Continued)

OTHER PUBLICATIONS

Dillard et al., "Evaluation of a Novel Intra–bronchial Valve Device to Produce Lung Volume Reduction," Poster shown at conference in Jun. 2002.

(Continued)

Primary Examiner—Manuel Mendez
(74) Attorney, Agent, or Firm—Knobbe, Martens, Olson & Bear LLP (57) ABSTRACT

The present invention includes an intra-bronchial device, system, and method for providing a therapeutic agent to a patient. A device includes a flow control member for placement in an air passageway communicating with a lung portion, and when deployed in the air passageway inhibits a therapeutic agent distal of the control member from moving proximal of the control member, and includes the therapeutic agent associated with the flow control member. The control member may inhibit movement of the therapeutic agent by limiting airflow, and may include a one-way valve limiting exhalation of air from the lung portion. The control member may include a flexible membrane impervious to air flow, or a separator arranged to inhibit the movement of the therapeutic agent. The control member may include at least one anchor, and the anchor may be releasable from the air passageway for removal of the intra-bronchial device.

16 Claims, 7 Drawing Sheets

U.S. PATENT DOCUMENTS

| | | |
|---|---|---|
| 4,212,463 A | 7/1980 | Repinski et al. |
| 4,250,873 A | 2/1981 | Bonnet |
| 4,302,854 A | 12/1981 | Runge |
| 4,710,192 A | 12/1987 | Liotta et al. |
| 4,732,152 A | 3/1988 | Wallsten et al. |
| 4,759,758 A | 7/1988 | Gabbay |
| 4,795,449 A | 1/1989 | Schneider et al. |
| 4,808,183 A | 2/1989 | Panje |
| 4,819,664 A | 4/1989 | Nazari |
| 4,830,003 A | 5/1989 | Wolff et al. |
| 4,832,680 A | 5/1989 | Haber et al. |
| 4,846,836 A | 7/1989 | Reich |
| 4,850,999 A | 7/1989 | Planck |
| 4,852,568 A | 8/1989 | Kensey |
| 4,877,025 A | 10/1989 | Hanson |
| 4,934,999 A | 6/1990 | Bader |
| 4,968,294 A | 11/1990 | Salama |
| 5,061,274 A | 10/1991 | Kensey |
| 5,116,360 A | 5/1992 | Pinchuk et al. |
| 5,116,564 A | 5/1992 | Jansen et al. |
| 5,123,919 A | 6/1992 | Sauter et al. |
| 5,151,105 A | 9/1992 | Kwan-Gett |
| 5,161,524 A | 11/1992 | Evans |
| 5,306,234 A | 4/1994 | Johnson |
| 5,352,240 A | 10/1994 | Ross |
| 5,358,518 A | 10/1994 | Camilli |
| 5,366,478 A | 11/1994 | Brinkerhoff et al. |
| 5,382,261 A | 1/1995 | Palmaz |
| 5,392,775 A | 2/1995 | Adkins, Jr. et al. |
| 5,409,019 A | 4/1995 | Wilk |
| 5,411,507 A | 5/1995 | Heckele |
| 5,411,552 A | 5/1995 | Andersen et al. |
| 5,413,599 A | 5/1995 | Imachi et al. |
| 5,417,226 A | 5/1995 | Juma |
| 5,445,626 A | 8/1995 | Gigante |
| 5,486,154 A | 1/1996 | Kelleher |
| 5,499,995 A | 3/1996 | Teirstein |
| 5,500,014 A | 3/1996 | Quijano et al. |
| 5,549,626 A | 8/1996 | Miller et al. |
| 5,549,628 A | 8/1996 | Cooper et al. |
| 5,562,608 A | 10/1996 | Sekins et al. |
| 5,645,565 A | 7/1997 | Rudd et al. |
| 5,660,175 A | 8/1997 | Dayal |
| 5,662,713 A | 9/1997 | Andersen et al. |
| 5,683,451 A | 11/1997 | Lenker et al. |
| 5,693,089 A | 12/1997 | Inoue |
| 5,697,968 A | 12/1997 | Rogers et al. |
| 5,702,409 A | 12/1997 | Rayburn et al. |
| 5,725,519 A | 3/1998 | Penner et al. |
| 5,752,965 A | 5/1998 | Francis et al. |
| 5,755,770 A | 5/1998 | Ravenscroft |
| 5,797,960 A | 8/1998 | Stevens et al. |
| 5,800,339 A | 9/1998 | Salama |
| 5,840,081 A | 11/1998 | Andersen et al. |
| 5,851,232 A | 12/1998 | Lois |
| 5,855,587 A | 1/1999 | Hyon et al. |
| 5,855,597 A | 1/1999 | Jayaraman |
| 5,855,601 A | 1/1999 | Bessler et al. |
| 5,944,738 A | 8/1999 | Amplatz et al. |
| 5,947,997 A | 9/1999 | Pavcnik et al. |
| 5,954,766 A | 9/1999 | Zadno-Azizi |
| 5,957,949 A | 9/1999 | Leonhardt et al. |
| 5,972,009 A | 10/1999 | Fortier et al. |
| 5,976,158 A | 11/1999 | Adams et al. |
| 5,976,174 A | 11/1999 | Ruiz |
| 5,984,965 A | 11/1999 | Knapp et al. |
| 6,003,517 A | 12/1999 | Sheffield et al. |
| 6,007,575 A | 12/1999 | Samuels |
| 6,009,614 A | 1/2000 | Morales |
| 6,020,380 A | 2/2000 | Killian |
| 6,027,525 A | 2/2000 | Suh et al. |
| 6,045,560 A | 4/2000 | McKean et al. |
| 6,051,022 A | 4/2000 | Cai et al. |
| 6,068,635 A | 5/2000 | Gianotti |
| 6,068,638 A | 5/2000 | Makower |
| 6,077,291 A | 6/2000 | Das |
| 6,083,255 A | 7/2000 | Laufer et al. |
| 6,096,027 A | 8/2000 | Layne |
| 6,099,551 A | 8/2000 | Gabbay |
| 6,123,663 A | 9/2000 | Rebuffat |
| 6,135,729 A | 10/2000 | Aber |
| 6,135,991 A | 10/2000 | Muni et al. |
| 6,141,855 A | 11/2000 | Morales |
| 6,162,245 A | 12/2000 | Jayaraman |
| 6,168,614 B1 | 1/2001 | Andersen et al. |
| 6,174,323 B1 | 1/2001 | Biggs |
| 6,183,520 B1 | 2/2001 | Pintauro et al. |
| 6,200,333 B1 | 3/2001 | Laufer |
| 6,206,918 B1 | 3/2001 | Campbell et al. |
| 6,234,996 B1 | 5/2001 | Bagaoisan et al. |
| 6,240,615 B1 | 6/2001 | Kimes et al. |
| 6,245,102 B1 | 6/2001 | Jayaraman |
| 6,258,100 B1 | 7/2001 | Alferness et al. |
| 6,270,527 B1 | 8/2001 | Campbell et al. |
| 6,287,290 B1 | 9/2001 | Perkins et al. |
| 6,287,334 B1 | 9/2001 | Moll et al. |
| 6,293,951 B1 | 9/2001 | Alferness et al. |
| 6,302,893 B1 | 10/2001 | Limon et al. |
| 6,312,407 B1 | 11/2001 | Zadno-Azizi et al. |
| 6,325,777 B1 | 12/2001 | Zadno-Azizi et al. |
| 6,325,778 B1 | 12/2001 | Zadno-Azizi et al. |
| 6,327,772 B1 | 12/2001 | Zadno-Azizi et al. |
| 6,328,689 B1 | 12/2001 | Gonzalez et al. |
| 6,355,014 B1 | 3/2002 | Zadno-Azizi et al. |
| 6,398,775 B1 | 6/2002 | Perkins et al. |
| 6,402,754 B1 | 6/2002 | Gonzalez |
| 6,416,554 B1 | 7/2002 | Alferness et al. |
| 6,428,561 B1 | 8/2002 | Johansson-Ruden et al. |
| 6,439,233 B1 | 8/2002 | Geertsema |
| 6,458,076 B1 | 10/2002 | Pruitt |
| 6,485,407 B2 | 11/2002 | Alferness et al. |
| 6,488,673 B1 | 12/2002 | Laufer |
| 6,491,706 B1 | 12/2002 | Alferness et al. |
| 6,493,589 B1 | 12/2002 | Medhkour et al. |
| 6,510,846 B1 | 1/2003 | O'Rourke |
| 6,514,290 B1 | 2/2003 | Loomas |
| 6,527,761 B1 | 3/2003 | Buch et al. |
| 6,585,639 B1 | 7/2003 | Kotmel et al. |
| 6,592,594 B2 | 7/2003 | Rimbaugh et al. |
| 6,599,311 B1 | 7/2003 | Biggs et al. |
| 6,610,043 B1 | 8/2003 | Ingenito |
| 6,629,951 B2 | 10/2003 | Laufer et al. |
| 6,634,363 B1 | 10/2003 | Danek et al. |
| 6,638,285 B2 | 10/2003 | Gabbay |
| 6,679,264 B1 | 1/2004 | Deem et al. |
| 2001/0025132 A1 | 9/2001 | Alferness et al. |
| 2001/0037808 A1 | 11/2001 | Deem et al. |
| 2001/0041906 A1 | 11/2001 | Gonzalez |
| 2001/0051799 A1 | 12/2001 | Ingenito |
| 2001/0052344 A1 | 12/2001 | Doshi |
| 2001/0056274 A1 | 12/2001 | Perkins et al. |
| 2002/0007831 A1 | 1/2002 | Davenport et al. |
| 2002/0062120 A1 | 5/2002 | Perkins et al. |
| 2002/0077593 A1 | 6/2002 | Perkins et al. |
| 2002/0077696 A1 | 6/2002 | Zadno-Azizi et al. |
| 2002/0087153 A1 | 7/2002 | Roschak et al. |
| 2002/0095209 A1 | 7/2002 | Zadno-Azizi et al. |
| 2002/0111619 A1 | 8/2002 | Keast et al. |
| 2002/0111620 A1 | 8/2002 | Cooper et al. |
| 2002/0112729 A1 | 8/2002 | DeVore et al. |
| 2002/0138135 A1 | 9/2002 | Duerig et al. |

| | | |
|---|---|---|
| 2002/0147462 A1 | 10/2002 | Mair et al. |
| 2003/0018327 A1 | 1/2003 | Truckai et al. |
| 2003/0018344 A1 | 1/2003 | Kaji et al. |
| 2003/0024527 A1 | 2/2003 | Ginn |
| 2003/0050648 A1 | 3/2003 | Alferness et al. |
| 2003/0051733 A1 | 3/2003 | Kotmel et al. |
| 2003/0055331 A1 | 3/2003 | Kotmel et al. |
| 2003/0070682 A1 | 4/2003 | Wilson et al. |
| 2003/0083671 A1 | 5/2003 | Rimbaugh et al. |
| 2003/0127090 A1 | 7/2003 | Gifford et al. |
| 2003/0154988 A1 | 8/2003 | DeVore et al. |
| 2003/0158515 A1 | 8/2003 | Gonzalez et al. |
| 2003/0228344 A1 | 12/2003 | Fields et al. |
| 2004/0039250 A1 | 2/2004 | Tholfsen et al. |

FOREIGN PATENT DOCUMENTS

| | | |
|---|---|---|
| WO | 94/26175 | 11/1994 |
| WO | 95/32018 | 11/1995 |
| WO | 96/34582 | 11/1996 |
| WO | 97/44085 | 11/1997 |
| WO | 98/00840 | 1/1998 |
| WO | 98/19633 | 5/1998 |
| WO | 98/39047 | 9/1998 |
| WO | 98/44854 | 10/1998 |
| WO | WO 98/048706 | 11/1998 |
| WO | 99/01076 | 1/1999 |
| WO | 99/13801 | 3/1999 |
| WO | 99/26692 | 6/1999 |
| WO | 99/32040 | 7/1999 |
| WO | 99/42059 | 8/1999 |
| WO | 99/42161 | 8/1999 |
| WO | 99/64109 | 12/1999 |
| WO | 00/42950 | 7/2000 |
| WO | 00/51510 | 9/2000 |
| WO | 00/62699 | 10/2000 |
| WO | 00/78386 | 12/2000 |
| WO | 00/78407 | 12/2000 |
| WO | 01/03642 | 1/2001 |
| WO | 01/05334 | 1/2001 |
| WO | WO 01/002042 | 1/2001 |
| WO | 01/10313 | 2/2001 |
| WO | 01/10314 | 2/2001 |
| WO | 01/12104 | 2/2001 |
| WO | WO 01/13839 | 3/2001 |
| WO | WO 01/013908 | 3/2001 |
| WO | 01/28433 | 4/2001 |
| WO | 01/45590 | 6/2001 |
| WO | 01/49213 | 7/2001 |
| WO | WO 01/052775 | 7/2001 |
| WO | 01/54585 | 8/2001 |
| WO | 01/54625 | 8/2001 |
| WO | 01/54685 | 8/2001 |
| WO | WO 01/066190 | 9/2001 |
| WO | 01/74271 | 10/2001 |
| WO | 01/89366 | 11/2001 |
| WO | WO 01/087170 | 11/2001 |
| WO | 02/05884 | 1/2002 |
| WO | WO 02/022072 | 3/2002 |
| WO | 02/32333 | 4/2002 |
| WO | 02/34322 | 5/2002 |
| WO | WO 02/038038 | 5/2002 |
| WO | 02/47575 | 6/2002 |
| WO | 02/056794 | 7/2002 |
| WO | 02/064045 | 8/2002 |
| WO | 02/064190 | 8/2002 |
| WO | WO 02/069823 | 9/2002 |
| WO | 02/094087 | 11/2002 |
| WO | 01/95766 | 12/2002 |
| WO | WO 03/022124 | 3/2003 |
| WO | WO 03/030975 | 4/2003 |
| WO | WO 03/034927 | 5/2003 |
| WO | WO 03/041779 | 5/2003 |
| WO | WO 03/047468 | 6/2003 |
| WO | 03/078579 | 9/2003 |
| WO | 03/088820 | 10/2003 |
| WO | 03/099164 | 12/2003 |
| WO | 04/010845 | 5/2004 |

OTHER PUBLICATIONS

EWS Endobronchial Watanabe Spigots, Novatech, edited Apr. 17, 2002.

Horiuchi et al; Three Cases of Intractable Pneumothorax Treated Successfully by Bronchial Embolization using Silicon; JJSB, 2001. pp. 25–30.

Inaspettato: Endoscopic Treatment of Bronchopleural Fistulas Using N–butyl–2–cyanoacrylate; Surgical Laparoscopy & Endoscopy; vol. 4 No. 1, pp. 62–64, 1994.

Jones et al: Closure of a Benign Broncho–Oesophageal Fistula by Endoscopic Injection of Bovine Collagen, Cyanocrylate Glue and Gelfoam; 1996, pp. 53–55 Aust. N.Z. J. Surg.

Okada et al: Emergent Bronchofiberoptic Bronchial Occlusion for Intractable Pneumothorax with Severe Emphysema; The Japanese Journal of Thoracic and Cardiovascular Surgery, 1998. pp. 1078–1081.

Watanabe et al: Bronchial Embolization Using Dental Impression Material in a Case of Pyelo–bronchial Fistula with Candida Fungemia; 1991. Journal of the Japan Society for Bronchology, pp. 607–610.

Harris et al., "The Experimental Production in Dogs of Emphysema with Associated Asthmatic Syndrome by Means of an Interatracheal Ball Valve," J. Exp Med 30:1919; 75–88.

Lewis et al., "Pulmonary Interstitial Emphysema: Selective Bronchial Occlusion with a Swan–Ganz Catheter." Archives of Disease in Childhood, 63:1988, 313–315.

Mathew et al. "Selective Bronchial Obstruction for Treatment of Bullous Interstitial Emphysema," J. of Ped. 96:1980, 475–477.

Puhakka et al., "Acute Bronchial Obstruction: An Experimental Rabbit Model Study." Int. J. Of Pediatric Otorhinolaryngology. 18:1989, 107–118.

Snider et al., "The Definition of Emphysema: Report of the National Heart Lung and Blood Institute, Division of Lung Diseases Workshop", Am. Rev. Respir. Dis., 132:182–185, 1985.

Article: Autocath®100—Nonsurgical, Intraurethral Bladder Control Device for Incontinent and Retentive Women—Dr. Kulisz's Development.

DEVICE AND METHOD FOR INTRA-BRONCHIAL PROVISION OF A THERAPEUTIC AGENT

RELATED APPLICATION

This application is a continuation-in-part of and claims priority based on United States applications entitled INTRA-BRONCHIAL AIRFLOW CONTROL DEVICE THAT CONTROLS BIOLOGICAL INTERACTION WITH THE PATIENT filed Feb. 21, 2002, application Ser. No. 10/081,712; and INTRA-BRONCHIAL AIRFLOW CONTROL DEVICE THAT CONTROLS BIOLOGICAL INTERACTION WITH THE PATIENT filed Jun. 21, 2002, application Ser. No. 10/178,073.

BACKGROUND OF THE INVENTION

There is a continuing need for improved minimally invasive delivery of therapeutic agents to all portions of the respiratory system, particularly the lungs, bronchi and bronchioli, blood vessels, and lymphatic system. There is also a continuing need for improved minimally invasive access to lung tissue and structures.

The airways in the lungs anatomically constitute an extensive network of conduits that reach all lung areas and lung tissues. The airways have extensive branching that distally communicates with the parenchyma alveoli where gas exchange occurs, and proximally with the trachea and atmosphere (air). Because of the physiological characteristics of the airways, a therapeutic agent placed in bronchi and bronchioli may be delivered focally, localized, or systemically depending on the agent and the manner in which it is placed.

Historically, there has been a limited use of airways for delivery of therapeutic agents, diagnostic procedures, and instrumentation for invasive procedures. The airways have successfully been used for delivery of certain small particle therapeutic agents, such as inhalers for asthma, administration of gas anesthesia, and for introduction of certain visual diagnostic tools in conjunction with a bronchoscope. Through the bronchoscope, a limited number of invasive procedures are now being performed, including biopsies and removal of foreign objects.

Treatment of certain lung diseases and conditions would benefit from targeted intra-bronchial delivery of therapeutic agents into the involved regions, particularly those associated with the lungs such as pneumonia and lung cancer. Treatment would be further benefited if the therapeutic agent is generally confined to the involved regions. For example, treatment of a disease such as pneumonia will benefit by being able to deliver an antibiotic to the specific lung region involved. Furthermore, treatment of lung cancer may benefit from non-invasive brachytherapy. However, the full potential use of the airways for delivery of therapeutic agents and invasive procedures has not been realized because current technology is not able to isolate selected portions of the airways and/or lung tissue where therapeutic agents or procedures are to be delivered.

In view of the foregoing, there is a need in the art for a new and improved device, system, and method for isolating selected portions of airways without adversely effecting lung function or structure while allowing delivery of a therapeutic agent, or instrumentation. However, no such device, system, or method presently exists. Aspects of the present invention are directed to providing such an improved device and method.

SUMMARY OF THE INVENTION

The present invention includes an intra-bronchial device, system, and method for providing a therapeutic agent to a patient. The invention provides an intra-bronchial device including a member arranged for placement in an air passageway, and a therapeutic agent associated with the member and arranged for provision to a patient. The member may be further arranged for inhibiting the therapeutic agent from moving proximal of the control member. The intra-bronchial device may further include at least one anchor that retains the intra-bronchial device within the air passageway when the anchor is deployed, and at least one anchor may be releasable from the air passageway for removal of the intra-bronchial device.

The invention also provides an assembly including a therapeutic agent arranged for intra-bronchial delivery into an air passageway of a patient, and a flow control member arranged for placement in the air passageway and inhibiting the therapeutic agent from moving proximal of the control member. The flow control member may be arranged to allow the therapeutic agent to be associated with the flow control member after the flow control member is placed in the air passageway. The flow control member may be arranged to allow the therapeutic agent to be placed into the air passageway distal of the flow control member after the flow control member is placed in the air passageway.

The invention further provides an intra-bronchial device for maintaining a therapeutic agent within an air passageway. The device includes a flow control member arranged for placement in the air passageway and inhibiting the therapeutic agent from moving proximal of the control member, and the therapeutic agent. The control member may inhibit movement of the therapeutic agent by limiting flow from the air passageway. The control member may inhibit movement of the therapeutic agent by limiting flow into the air passageway, which limitation may be by limiting mucociliary transport from the air passageway. The control member may include a one-way valve. The one-way valve may permit inhalation of air into the air passageway, or permit exhalation of air from the air passageway. The control member may include a flexible membrane impervious to air flow. The flexible membrane may be arranged in cooperation with a wall of the air passageway to form a one-way valve permitting airflow from the air passageway, or a one-way valve permitting airflow into the air passageway. The control member may include a separator arranged to inhibit the movement of the therapeutic agent while allowing movement of air. The molecules of the therapeutic agent may be associated with molecules larger than air molecules, and the separator arranged to inhibit movement of the associated molecules while allowing movement of air molecules. The control member may include a semi-permeable membrane arranged to retain the therapeutic agent distal of the control member while permitting air and water molecules to be exhaled. The control member may limit airflow from the air passageway sufficiently to maintain inflation of a lung portion communicating with the air passageway. The control member may allow airflow from the air passageway sufficiently to prevent over-inflation of the lung portion. The control member may further include at least one anchor that retains the intra-bronchial device within the air passageway when the anchor is deployed, and at least one anchor may be releasable from the air passageway for removal of the intra-bronchial device. The control member may be further arranged to automatically terminate the inhibiting of movement by the therapeutic agent. The automatic termination may be provided by deterioration of the control member, or by dissolution of the control member.

The control member may be further arranged to permit mucociliary transport from the air passageway. The therapeutic agent may be associated with at least a portion of the control member. The therapeutic agent may overlie at least a portion of the airflow control member, may be imbedded in at least a portion of the airflow control member, may be absorbed in at least a portion of the airflow control member, and/or may be co-mixed with at least a portion of the airflow control member. The control member further includes an absorptive member and the therapeutic agent is absorbed by the absorptive member. The control member may include a cavity, and the therapeutic agent carried in the cavity. The cavity may include an absorptive member, and the therapeutic agent absorbed by the absorptive member. The cavity may included a cover having an orifice. The therapeutic agent may be one of antimicrobial agents such as adrenergic agents, antibiotic agents or antibacterial agents, antiviral agents, anthelmintic agents, anti-inflammatory agents, antineoplastic agents, antioxidant agents, biological reaction inhibitors, botulinum toxin agents, chemotherapy agents, diagnostic agents, gene therapy agents, hormonal agents, mucolytic agents, radioprotective agents, radioactive agents including brachytherapy materials, tissue growth inhibitors, tissue growth enhancers, and vasoactive agents.

The invention still further provides a system for intra-bronchially providing a therapeutic agent to a patient. The system includes an intra-bronchial device including a flow control device arranged for placement in an air passageway, and when deployed, limits flow from the air passageway sufficiently to inhibit a therapeutic agent distal of the control member from moving proximal, and an introducer that introduces the therapeutic agent in the lung portion distal of the airflow control member.

The invention yet still further provides a method for providing a therapeutic agent to a patient. The method may include the steps of delivering a therapeutic agent to a lung portion, and inhibiting movement of the therapeutic agent from the lung portion. The inhibiting step may include the further step of limiting airflow from the lung portion to inhibit therapeutic agent distal of the control member from moving proximal. The method may include the further step of maintaining an inflation of the lung portion. The method may include the further step of maintaining a collapse of the lung portion. The delivering step may be performed with one intra-bronchial device and the inhibiting step is performed with another intra-bronchial device. The method may include the further step of performing the delivering step again. The inhibiting step may include the further step of implanting an intra-bronchial device in an air passageway in communication with the lung portion. The delivery step may include providing the therapeutic agent to the intra-bronchial device. The method may include the further step of terminating the inhibition of movement. The therapeutic agent may be one of antimicrobial agents such as adrenergic agents, antibiotic agents or antibacterial agents, antiviral agents, anthelmintic agents, anti-inflammatory agents, antineoplastic agents, antioxidant agents, biological reaction inhibitors, botulinum toxin agents, chemotherapy agents, diagnostic agents, gene therapy agents, hormonal agents, mucolytic agents, radioprotective agents, radioactive agents including brachytherapy materials, tissue growth inhibitors, tissue growth enhancers, and vasoactive agents.

The invention also provides an intra-bronchial device for providing a therapeutic agent to a patient. The device including means for delivering a therapeutic agent into an air passageway of the patient, and means for intra-bronchially inhibiting movement of the therapeutic agent from the air passageway. The movement may be inhibited by limiting exhalation from the air passageway, by limiting inhalation into the air passageway, and/or by limiting movement of mucus from the air passageway.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawings, in the several figures of which like referenced numerals identify identical elements, and wherein:

FIG.

DETAILED DESCRIPTION OF THE PREFERRED EMBODIMENTS

In the following detailed description of exemplary embodiments of the invention, reference is made to the accompanying drawings that form a part hereof. The detailed description and the drawings illustrate specific exemplary embodiments by which the invention may be practiced. These embodiments are described in sufficient detail to enable those skilled in the art to practice the invention. It is understood that other embodiments may be utilized, and other changes may be made, without departing from the spirit or scope of the present invention. The following detailed description is therefore not to be taken in a limiting sense, and the scope of the present invention is defined by the appended claims.

Throughout the specification and claims, the following terms take the meanings explicitly associated herein unless the context clearly dictates otherwise. The meaning of "a", "an", and "the" include plural references. The meaning of "in" includes "in" and "on." Referring to the drawings, like numbers indicate like parts throughout the views. Additionally, a reference to the singular includes a reference to the plural unless otherwise stated or inconsistent with the disclosure herein. Additionally, throughout the specification, claims, and drawings, the term "proximal" means nearest the trachea, and "distal" means nearest the alveoli.

Figure 1:
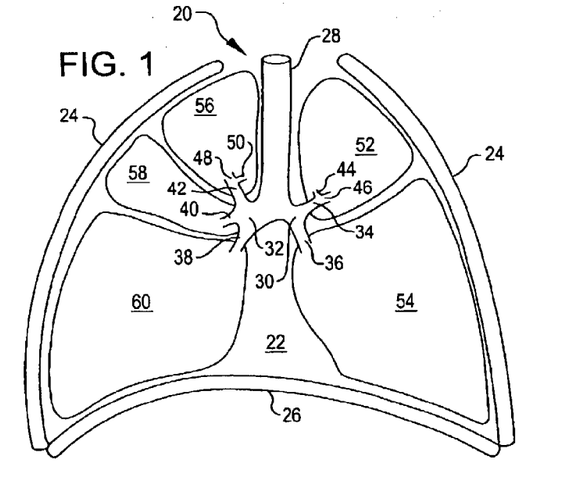

FIG. 1 is a sectional view of a healthy respiratory system. The respiratory system 20 resides within the thorax 22 that occupies a space defined by the chest wall 24 and the diaphragm 26.

Figure 2:
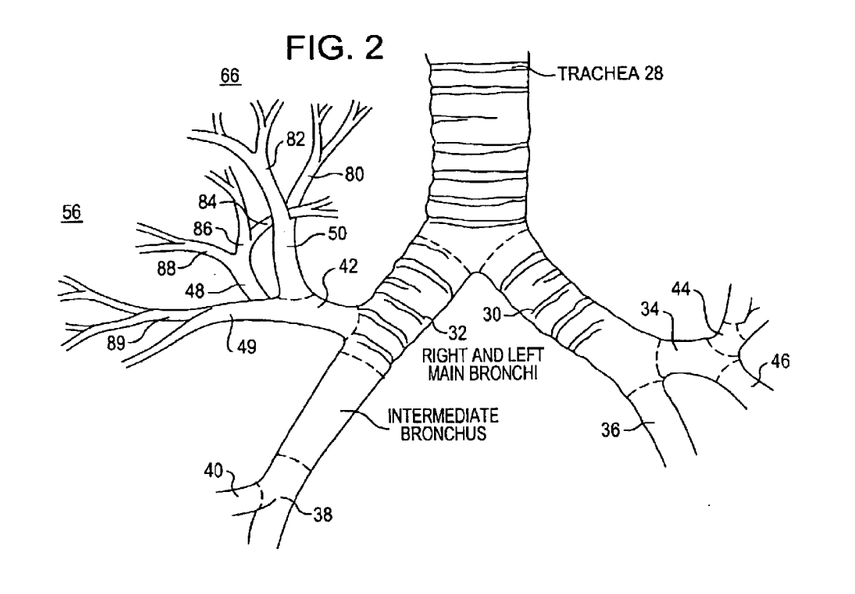
Figure 3:
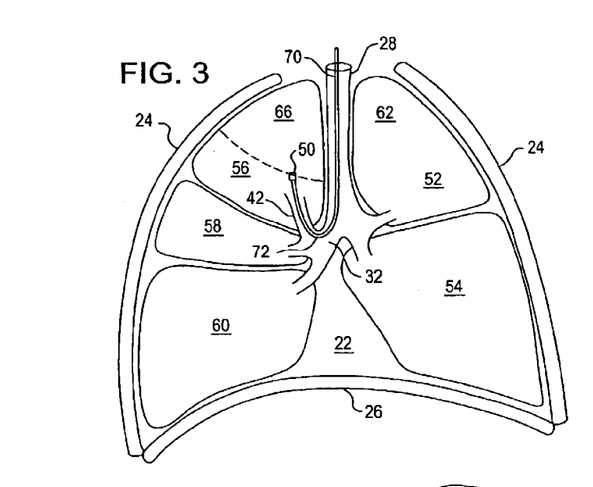

The respiratory system 20 includes trachea 28; left mainstem bronchus 30 and right mainstem bronchus 32 (primary, or first generation); and lobar bronchial branches 34, 36, 38, 40, and 42 (second generation). FIG. 1 also illustrates segmental branches 44, 46, 48, 49, and 50 (third generation). Additional sub-branches are illustrated in FIG. 2. The respiratory system 20 further includes left lung lobes 52 and 54 and right lung lobes 56, 58, and 60. Each bronchial branch and sub-branch communicates with a different portion of a lung lobe, either the entire lung lobe or a portion thereof. As used herein, the term "air passageway" is meant to denote either a bronchi or bronchioli, and typically means a bronchial branch of any generation.

A characteristic of a healthy respiratory system is the arched or inwardly arcuate diaphragm 26. As the individual inhales, the diaphragm 26 straightens to increase the volume of the thorax 22. This causes a negative pressure within the thorax. The negative pressure within the thorax in turn causes the lung lobes to fill with air. When the individual exhales, the diaphragm returns to its original arched condition to decrease the volume of the thorax. The decreased volume of the thorax causes a positive pressure within the thorax, which in turn causes exhalation of the lung lobes.

Another characteristic of the respiratory system is the mucus flow from the lungs, or mucociliary transport system. Many pollution particles are inhaled as a person breathes, and the air passageways function as a very effective filter. The mucociliary transport system functions as a self-cleaning mechanism for all air passageways, including the lungs. The mucociliary transport system is a primary method for mucus clearance from distal portions of the lungs, and further constitutes a primary immune barrier for the lungs. The surface of air passageways is formed with respiratory epithelium (or epithelial membrane), which is covered with cilia and coated with mucus. As part of the mucociliary transport system, the mucus entraps many inhaled particles and moves them toward the larynx 28. The mucociliary transport system includes the metachronal ciliary beat of cilia on the respiratory epithelium that moves a continuous carpet of mucus and entrapped particles from the distal portions of the lungs past the larynx 28 and to the pharynx for expulsion from the respiratory system. The mucociliary transport system will also function as a self-clearing mechanism removing therapeutic agents placed in a lung portion and entrapped by the mucus. Additional description of the mucociliary transport system is provided in INTRA-BRONCHIAL OBSTRUCTING DEVICE THAT PERMITS MUCUS TRANSPORT filed May 9, 2002, application Ser. No. 10/143,353, which is owned by the Assignee, and which is incorporated herein by reference.

FIG. 2 is a perspective view of the bronchi emphasizing the upper right lung lobe 56. In addition to the bronchial branches illustrated in FIG. 1, FIG. 2 illustrates subsegmental bronchial branches 80, 82, 84, 86, 88, and 89 (fourth generation) providing air circulation to superior right lung lobe 56. The fifth- and sixth-generation bronchial branches are illustrated, but not given reference numbers.

The air passageways branch out, much like the roots of a tree. The bronchial segments branch into six generations or orders, and the bronchioles branch into approximately another three to eight generations or orders. Typically, each generation has a smaller diameter than its predecessor. The inside diameter of a generation varies depending on the particular bronchial branch, and further varies between individuals. For example, a typical lobar bronchus 42 (third generation) providing air circulation to the upper right upper lobe 56 has an internal diameter of approximately 1 cm. A typical segmental bronchi 48 (fourth generation) has an internal diameter of approximately 4 to 7 mm. The fifth and sixth generations (no reference numbers) are each proportionately smaller. The bronchial segments include annular ligaments and irregularly located cartilages that provide structure and resilience. The cartilages become increasingly sparse as the bronchial segments become smaller in diameter. The bronchioles do not have ligaments and cartilages. Furthermore, the inside diameters of air passageways is not static. They expand when a person inhales and contract when a person exhales.

FIGS. 3–7 illustrate a series of steps in providing a therapeutic agent to a patient, in accordance with the invention. FIG. 3 illustrates an initial step that includes placing an intra-bronchial device in an air passageway 50 using a catheter or bronchoscope. The invention disclosed herein is not limited to use with the particular method illustrated herein, and may be used in any air passageway or body lumen. Catheter 70 may be used alone to perform the insertion, may be extended from a bronchoscope, or used in conjunction with a bronchoscope. For purposes of this description, the insertion will be described with reference to only the catheter 70. Provision of a therapeutic agent is initiated by feeding a conduit, such as a catheter 70 down the trachea 28, into the right mainstem bronchus 32, into the bronchial branch 42 and into and terminating within the sub-branch 50. The sub-branch 50 is the air passageway that communicates with the lung portion 66 to be treated. The catheter 70 is preferably formed of flexible material such as polyethylene. Also, the catheter 70 is preferably preformed with a bend 72 to assist the feeding of the catheter from the right mainstem bronchus 32 into the bronchial branch 42, or could be deformed to conform to different curvature and angles of a bronchial tree.

Figure 4:
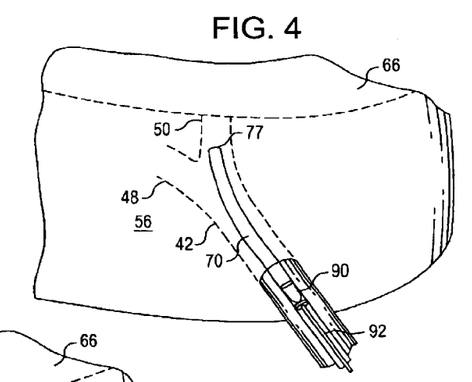

FIG. 4 illustrates a further step in placing a flow control member 90 of the intra-bronchial device in a bronchial sub-branch 50 using a catheter or a bronchoscope. The control member 90 may be formed of resilient or collapsible material to enable the control member 90 to be fed through the conduit 70 in a collapsed state. A stylet 92 is used to push the control member 90 to the end 77 of the catheter 70 for inserting the control member 90 within the air passageway 50 adjacent to the lung portion 66 to be provided with the therapeutic agent.

Figure 5:
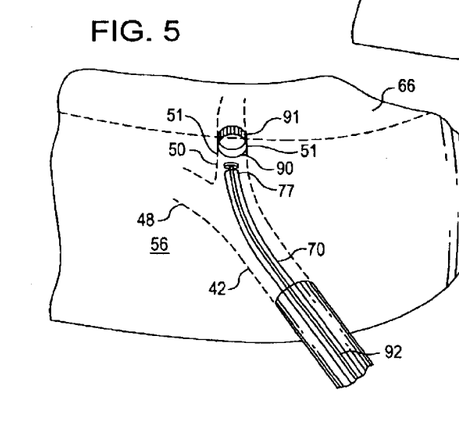

FIG. 5 illustrates an intermediate step where the flow control member 90 has been inserted in air passageway 50, in accordance with the invention. Flow control member 90 has been pushed from the end 77 of the catheter 70 and expanded upon placement in the air passageway 50 to limit exhalation airflow and mucus flow (mucociliary transport) from the lung portion 66. This causes the lung portion 66 to be maintained in an expanded state. Because the exhalation airflow and the mucus flow (mucociliary transport) are limited, any therapeutic agent distal of the flow control member 90 will be inhibited from moving proximal of control member 90 and substantially confined to the lung portion 66 for provision of therapy.

Figure 6:
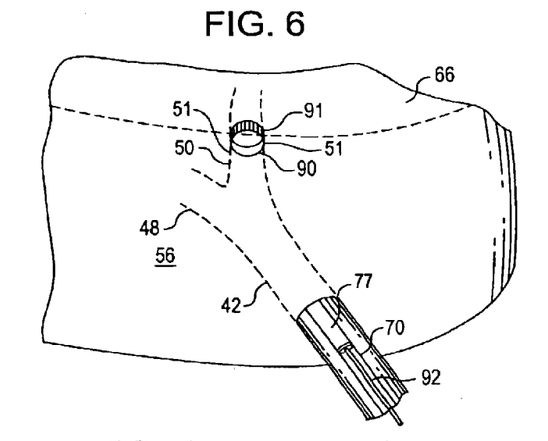

FIG. 6 illustrates a final step in inserting a flow control member 90 of the intra-bronchial device, in accordance with the invention. The catheter 70 and the stylet 92 are being withdrawn from the patient, leaving the expanded flow control member 90 in air passageway 50.

The control member 90 may be any shape and composed of any material suitable for accomplishing its purpose. Possible shapes include spherical, cylindrical, oval, and conical. For example, control member 90 may be a conical shaped plug arranged to inhibit proximal movement of a therapeutic agent by sealing air passageway 50 against proximal flow of air and mucus. Control member 90 may be a solid member, a composition of materials, or a membrane that retains a shape or is carried on a frame. More specifically, the control member 90 has an outer dimension 91, and when expanded, enables contact with an air passageway inner dimension 51. The contact may be arranged in any manner to inhibit a therapeutic agent distal of the control member 90 from moving proximal to control member 90. As used in this specification, including the description and claims, the meaning of word "inhibit" and its derivatives, such as "inhibiting," include reducing, diminishing, hindering, restraining, preventing, precluding, or prohibiting, unless otherwise indicated.

The intra-bronchial device is described in this specification, including the detailed description and the claims, in terms of limiting flow from a lung portion communicating with an air passageway. In some lungs, a portion of a lung may receive air from collateral air passageways. Controlling the airflow or mucociliary transport in one of the collateral air passageways may reduce the flow from the lung portion communicating with that air passageway, but may not completely control flow from the lung portion.

Figure 7:
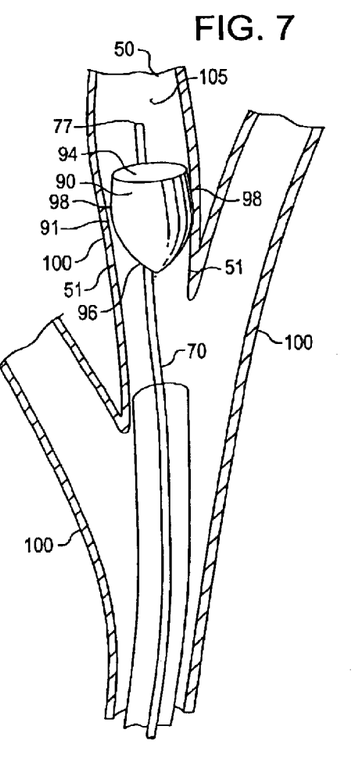

FIG. 7 is a longitudinal sectional view illustrating releasing a therapeutic agent 105 distal of control member 90, in accordance with the invention. In this embodiment, control member 90 generally has conical configuration, and may be hollow. More specifically, the control member 90 includes a periphery that renders it generally circular at its base, referred to herein as generally circular base 94. The control member 90 further includes a circumferential, generally conical sidewall 96 that extends from the outer periphery of generally circular base 94. The sidewall 96 has an exterior perimeter surface 98 that defines the outer periphery 91 of the control member 90. The control member 90 is arranged so that the outer periphery 91 of its exterior perimeter surface 98 contacts the air passageway inner dimension 51 of bronchial wall 100 to form a seal that limits air and/or mucus from moving past control member 90. The degree of inhibition may be varied by changing the structure of the control member 90.

Once the control member 90 is paced in the air passageway 50, a final step includes releasing the therapeutic agent 105 distal of the control member 90. Catheter 70 may be used to discharge therapeutic agent 105, or another thin catheter arranged for delivery of the therapeutic agent 105 may be used. The tip 77 of catheter 70 is guided between the exterior perimeter surface 98 and the bronchial wall 100, and advanced until tip 77 is distal of control member 90. The therapeutic agent 105 is released from the tip 77, and the catheter 70 is withdrawn from the patient. Additional doses of the therapeutic agent 105 may be administered by again placing a delivery catheter in the air passageway 50 and releasing additional therapeutic agent 105 distal of the control member 90.

In an alternative embodiment, the therapeutic agent 105 may be released first, and the control member 90 then placed in the air passageway 50 in position to inhibit movement of the therapeutic agent 105. In a further alternative embodiment, the control member 90 may be made of a self-sealing, pierceable material, such as a membrane, and the tip 77 arranged to pierce through the control member 90 and discharge the therapeutic agent 105 distal of the control member 90. In yet a further embodiment, the control member 90 may include an absorbable material, and the tip 77 arranged to discharge the therapeutic agent 105 into the absorbable material for release from the absorbable material distal of the control member 90.

In another embodiment, control member 90 may include a plurality of longitudinal ribs (not shown) on the outer peripheral surface 91. When the control member 90 is placed in the air passageway 50, the ribs and the interior wall of the air passageway define at least one peripheral flow pathway. The dimensioning and spacing of the longitudinal ribs may be selected to define the size of the peripheral flow pathway, and the degree to which airflow and/or mucociliary transport are inhibited. The larger a flow pathway, the less a flow will be limited.

In a still further alternative embodiment, the control member 90 is arranged to automatically terminate inhibition of proximal movement of the therapeutic agent 105. The inhibition may be automatically terminated by a dissolving, deteriorating, or other structural characteristic that causes the control member 90 to terminate forming a seal with the air passageway wall 100 without any outside act or step being taken. For example, all or a portion of the control member 90 may be made from a foam material arranged to dissolve or deteriorate after a predetermined length of time. Alternatively, all or a portion of control member 90 may be made from a sugar that will dissolve after a predetermined length of time. By way of further example, control member 90 may be arranged to dissolve or deteriorate after several days in the air passageway 50. This could allow treatment of localized pneumonia by isolating the involved lung portion with the control member 90. An antibiotic agent suitable for treating pneumonia may be placed in the lung portion 66, and retained in the lung portion by control member 90 for several days. After that period of time, the control member 90 would automatically deteriorate or dissolve, and be removed from the air passageway 50 by absorption, mucociliary transport, coughing, or some other mechanism without outside action. This would terminate the isolation and return the lung portion to normal functioning.

The term "therapeutic agent" is broadly used in this specification, including the description and claims, and includes anything presented for treatment, curing, mitigating, or preventing deleterious conditions in humans and animals. The term "therapeutic agent" also includes substances and agents for combating a disease, condition, or disorder of a patient, and includes drugs, diagnostics, and instrumentation.

"Therapeutic agent" also includes anything used in medical diagnosis, or in restoring, correcting, or modifying physiological functions. The term "therapeutic agent" may also mean a medicant or a medicine.

The therapeutic agent is selected according to the treatment objective and biological action desired. General classes of therapeutic agents include anti-microbial agents such as adrenergic agents, antibiotic agents or antibacterial agents, antiviral agents, anthelmintic agents, anti-inflammatory agents, antineoplastic agents, antioxidant agents, biological reaction inhibitors, botulinum toxin agents, chemotherapy agents, diagnostic agents, gene therapy agents, hormonal agents, mucolytic agents, radioprotective agents, radioactive agents including brachytherapy materials, tissue growth inhibitors, tissue growth enhancers, and vasoactive agents.

The therapeutic agent may be selected from any class suitable for the therapeutic objective. For example, if the objective is treating a disease or condition associated with lungs such as acute or chronic pneumonia, the therapeutic agent may include antibiotics such as penicillin, ceftriaxone, tobramycin, vancomycin. By way of further example, if the desired treatment objective is treatment of cancer in lung or nearby tissue, the therapeutic agent may include radioactive material in the form of radioactive seeds providing radiation treatment directly into the tumor or close to it. Further, the therapeutic agent may be selected or arranged to provide therapeutic activity over a period of time.

Figure 8:
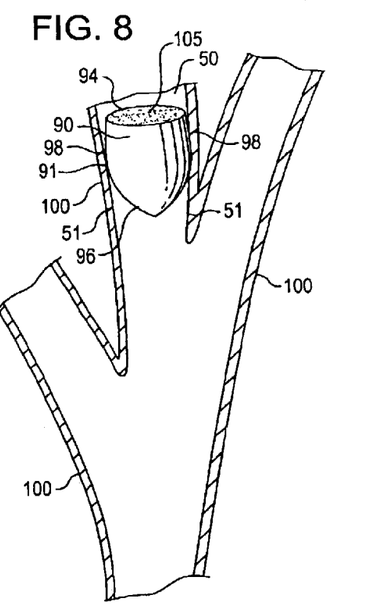

FIG. 8 is a longitudinal sectional view illustrating an intra-bronchial device placed in an air passageway 50 for providing a therapeutic agent 105 to a patient, where the therapeutic agent 105 is associated with a control member 90, in accordance with the invention. For purposes of clarity in the specification and drawings, embodiments of the invention are generally illustrated with control member 90 as the only element of the intra-bronchial device. Alternative embodiments of an intra-bronchial device according to an aspect of the invention may include additional elements, such as structural members, anchors, and other members.

Figure 15:
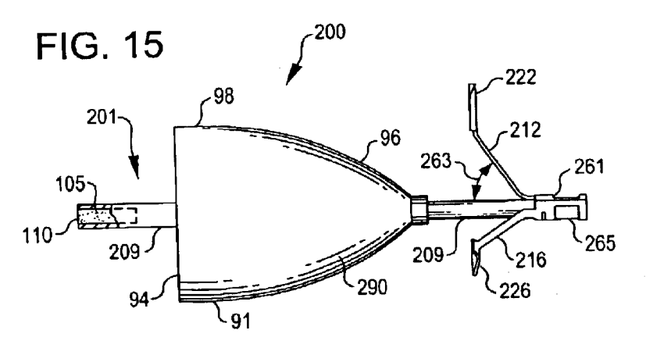
Figure 16A:
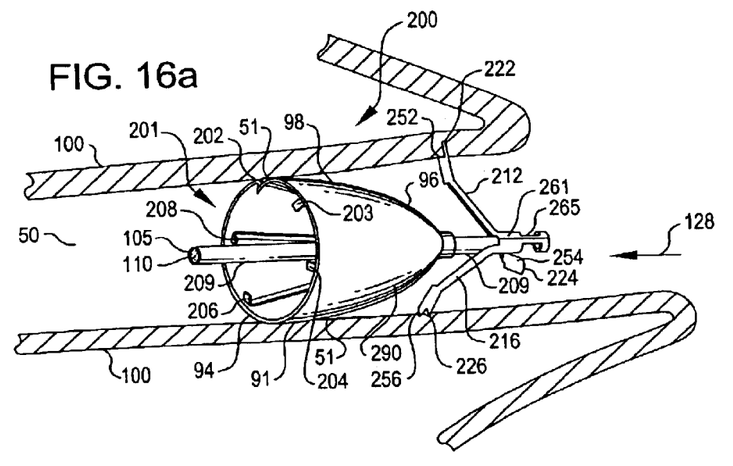
Figure 16B:
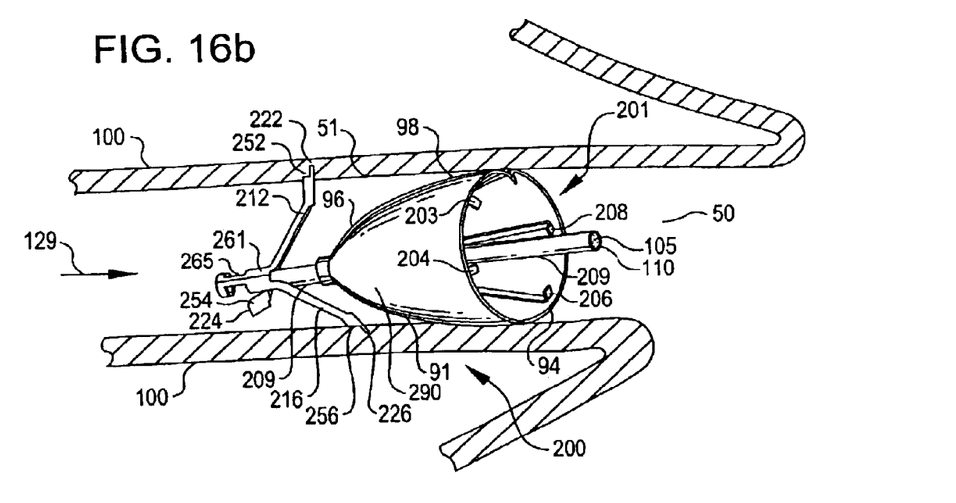

In accordance with a broad aspect of the present invention, the therapeutic agent 105 may be associated with the control member 90 of an intra-bronchial device in any manner known in the art suitable for release or provision to the patient. An embodiment of the invention is arranged to release of therapeutic agent 105 distal of the intra-bronchial device for providing focal and systemic treatments. Other embodiments are arranged to provide the therapeutic agent 105 to the tissue contact area between the intra-bronchial and the wall of the air passageway 100. FIG. 8 illustrates an embodiment where the therapeutic agent 105 is directly carried by or associated with the intra-bronchial device for release and provision to the patient. Alternatively, the therapeutic agent may be carried by or associated with another element that is coupled to the control member 90 as illustrated in FIGS. 15 and 16. The therapeutic agent 105 may be associated with the control member 90 in many different ways. It may be carried on proximal, distal, or both proximal and distal portions of the device as may be required by the intended therapeutic action and limitations of the selected therapeutic agent. FIG. 8, for example, illustrates an embodiment where therapeutic agent 105 overlies the surface of generally circular base 94 of control member 90. If the control member 90 is a membrane or generally hollow structure, the therapeutic agent 105 may be associated by overlayment on any suitable surface or surfaces, including an interior surface, or by another member coupled to the control member 90.

Therapeutic agent 105 may be associated with all or any portion of the control member 90 in any manner known to those skilled in the art, and as required by the therapeutic action desired and the limitations of the selected therapeutic agent 105. Association methods include overlayment, absorption, and imbedding, which may be by any method known to those in the art, including spraying, dipping, ion implantation, and painting. Alternative embodiments of the invention may include associating therapeutic agent 105 by impregnation, co-mixing, or absorption into control member 90 in any manner known to those skilled in the art, and as required by therapeutic action desired and the limitations of the selected therapeutic agent 105. Co-mixing includes combining the therapeutic agent 105 with a carrier or the material of control member 90 in such a manner that the therapeutic agent 105 is releasable from the mix. An anti-microbial therapeutic agent 105 may be absorbed into at least a portion of control member 90.

An aspect of the invention and a flow control member, such as control member 90, is directed toward targeted intra-bronchial delivery of a therapeutic agent that treats diseases and conditions of the patient, particularly those associated with the lungs such as inflammatory, infectious, and neoplastic diseases. Treatment of certain lung diseases and conditions will benefit from targeted intra-bronchial delivery of a therapeutic agent 105 into the involved regions. Treatment will be further benefited if the therapeutic agent 105 is generally confined to the involved regions. For example, treatment of pneumonia will benefit by being able to deliver an antibiotic to the specific lung region involve. Treatment will also be benefited by isolating the involved lung portion to prevent disease dissemination. By inhibiting exhalation and/or mucociliary transport, control member 90 meets these treatment goals by generally confining the therapeutic agent to the lung portion, and by isolating the lung portion to prevent disease dissemination. Depending on the course of treatment desired, control member 90 may be arranged to allow the lung portion to be or remain inflated by allowing inhalation airflow and limiting exhalation airflow, or to collapse the lung portion by limiting inhalation airflow.

Still further, the therapeutic agent may be associated with an element of an intra-bronchial device, which in turn is coupled to control member 90. Such elements may include structural members, or anchors for example. The therapeutic agent may be associated with control member 90 either before or after it is inserted into air passageway 50, or renewed after insertion.

Figure 9:
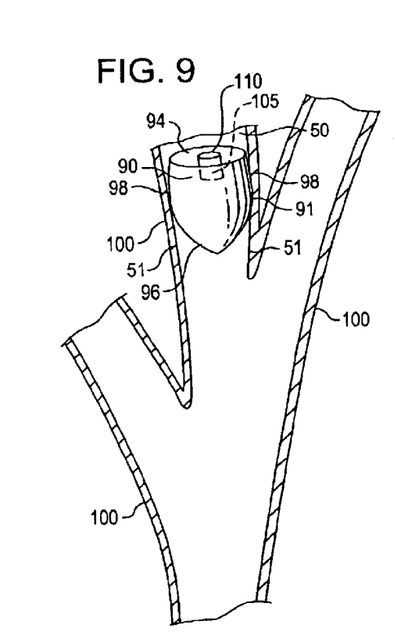

FIG. 9 is a longitudinal sectional view illustrating an intra-bronchial device placed in an air passageway 50 for providing a therapeutic agent 105 to a patient, the control member 90 of the intra-bronchial device having a cavity 110 for carrying the therapeutic agent 105, in accordance with the invention. Control member 90 includes a cavity 110 that carries therapeutic agent 105. While the cavity 110 is illustrated in FIG. 9 as cylindrical in configuration, it may be of any shape. Radioactive seeds may be carried in cavity 110. A plurality of intra-bronchial devices may be placed in a lung portion, thus allowing providers to group or cluster the radioactive seeds in a manner similar to that used to treat tumors in other portions of the body, such as prostate, breast, and brain tumors.

In another embodiment, the cavity 110 of control member 90 may include an absorptive member (not shown) that carries the therapeutic agent 105. The absorptive member may occupy all or at least a portion of the cavity 110. The absorptive member may be any material and any configuration known to those skilled in the art, and as required by the limitations of selected therapeutic agent 105.

Figure 10:
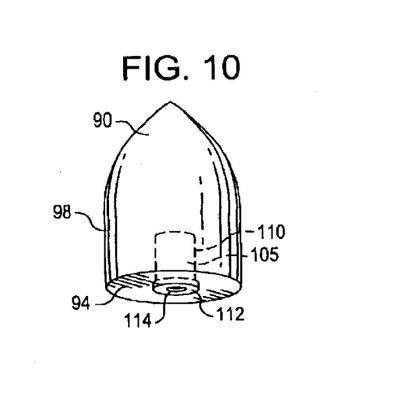

FIG. 10 illustrates a control member 90 similar to FIG. 9 with a cover 112 having an orifice 114 to regulate release of the therapeutic agent 105, in accordance with the invention. The orifice 114 of cavity cover 112 limits the release of the therapeutic agent 105 from cavity 110. Orifice 114 is sized and located to regulate the release of therapeutic agent from cavity 110.

Figure 11:
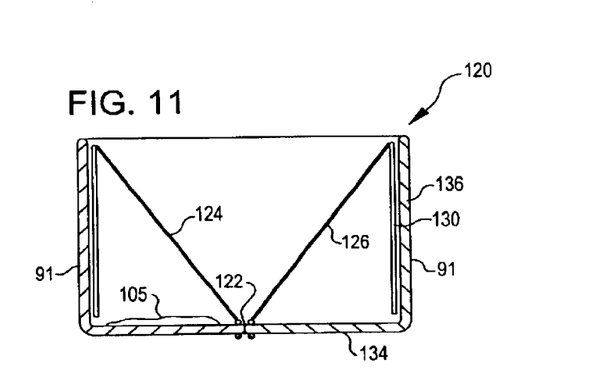
Figure 12:
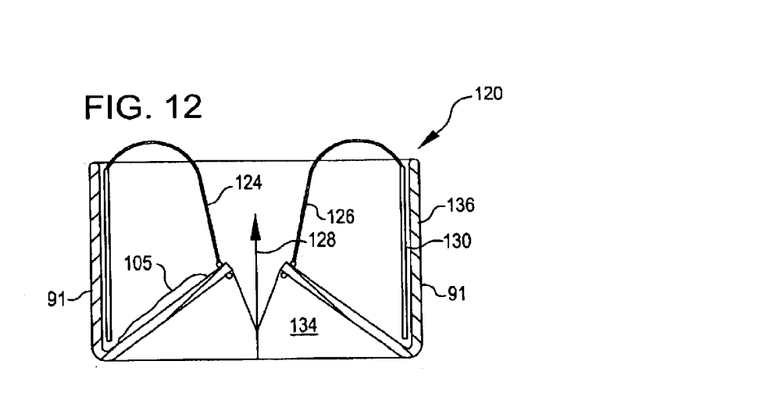
Figure 13:
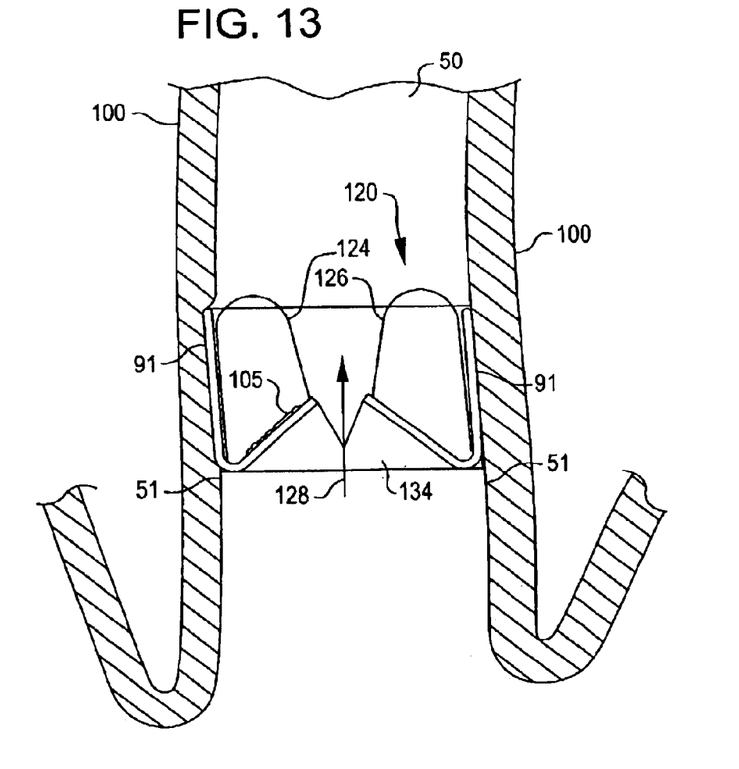

FIGS. 11–13 illustrate an intra-bronchial device for providing a therapeutic agent 105 with a control member 120 having a one-way valve, in accordance with the invention. FIG. 11 illustrates the control member 120 with the one-way valve in a closed configuration, and FIG. 12 illustrates the one-way valve in an open configuration. Control member 120 includes a structure similar to that described in U.S. Pat. No. 6,293,951, which is owned by the assignee of this application, and which is incorporated herein by reference. However, the control member 120 and one-way valve of the instant invention are structured and arranged when deployed in an air passageway to permit inhalation of air into the lung portion while inhibiting exhalation of air from the lung portion.

The one-way valve may be centrally positioned in the control member 120. Control member 120 includes a generally circular base 134 and a circumferential generally cylindrical sidewall 136. Control member 120 further includes resilient reinforcement rib 130. To form the one-way valve, the base 134 is made from a resilient material, and includes a slit 122 to form a valving structure. On either side of the slit 122 is a tether 124 and 126, which extend to the resilient reinforcement rib 130. As illustrated in FIG. 13, control member 120 is configured for placement in the air passageway 50 so that the one-way valve structure opens to permit inhalation airflow 128 (in the direction indicated by the arrow), and closes to limit exhalation airflow. The therapeutic agent 105 is associated with the control member 120 as described in conjunction with FIG. 8.

FIG. 13 is a longitudinal sectional view illustrating the intra-bronchial device placed in the air passageway 50. The intra bronchial device may be placed in the air passageway 50 using any method known to those skilled in the art, including the method described in conjunction with FIGS. 3–6. The one-way valve structure opens to permit inspiration airflow 128 (in the direction indicated by the arrow), but limits exhalation airflow. This orientation permits air to be inhaled into the distal lung portion, which may assist in delivering the therapeutic agent 105 to the distal lung portion communicating with the air passageway 50. Conversely, the one-way valve may be arranged to permit exhaustion airflow but preclude inspiration, if advantageous.

The contact between the outer dimension 91 and air passageway inner dimension 51 may be arranged to form a mucus seal stopping or limiting proximal mucus movement. The one-way valve will limit airflow from the lung portion 66 and maintain it in an inflated condition. Any therapeutic agent 105 released distally of control member 90 will be inhibited from moving proximally by the one-way valve and the mucus seal.

An aspect of the invention provides for arranging and carrying therapeutic agent 105 on a distal portion of a control member in a manner to promote intra-bronchial delivery. FIG. 13 illustrates therapeutic agent 105 associated with a distal portion of base 134 of control member 120, which also forms a moveable part of the valve. In this structural arrangement, therapeutic agent 105 is physically exposed to the targeted distal lung portion, and movement of the valve with inhalation 128 and against exhalation may aid release of therapeutic agent 105. The structure of control member 120 will inhibit the released therapeutic agent 105 from moving proximally, although therapeutic agent 105 may move proximal to the control member by escaping through the valve, between the wall 100 and control member 120, or by mucociliary transport.

Figure 14:
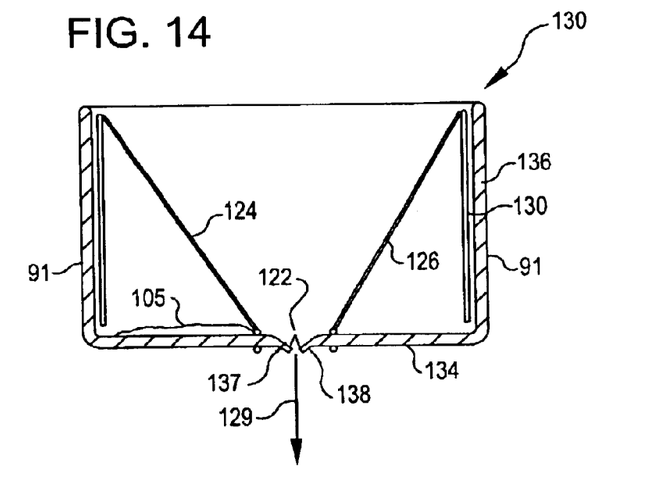

FIG. 14 is a longitudinal sectional view illustrating an alternative embodiment of the intra-bronchial device of FIGS. 11–13 having a valving mechanism arranged to open when the air pressure in the lung portion reaches a predetermined level and to allow exhalation airflow to prevent over inflation of the lung portion, in accordance with the invention. Control member 130 is substantially similar to control member 120, however, the fixation points of the tethers 124 and 126 has been moved radially away from the slit 122, and the thickness of portions of the base 134 proximate to the slit 122 has been reduced to provide lips 137 and 138. The lips 137 and 138 are arranged to open when the air pressure in the lung portion reaches a predetermined level and to allow exhalation airflow 129 (in the direction indicated by the arrow) to prevent over inflation of the lung portion.

FIGS. 15, 16a, and 16b illustrate an anchored intra-bronchial device 200 for providing a therapeutic agent 105, in accordance with the invention. Intra-bronchial device 200 includes a flow control member 290 and distal anchors carried on a central support structure. FIG. 15 is a side view of the device 200. FIG. 16a illustrates the device 200 placed in an air passageway with an orientation that permits inhalation airflow 128 and inhibits exhalation flow, and FIG. 16b illustrates the device 200 with an orientation that permits exhalation airflow 129 and inhibits inhalation air flow. Anchored and removable intra-bronchial devices are disclosed in co-pending applications "REMOVABLE LUNG REDUCTION DEVICES, SYSTEMS, AND METHODS" filed Sep. 11, 2001, application Ser. No. 09/951,105; "REMOVABLE ANCHORED LUNG VOLUME REDUCTION DEVICES AND METHODS" filed Mar. 20, 2002, application Ser. No. 10/104,487; "REMOVABLE ANCHORED LUNG VOLUME REDUCTION DEVICES AND METHODS" filed Apr. 16, 2002, application Ser. No. 10/124,790; and "REMOVABLE ANCHORED LUNG VOLUME REDUCTION DEVICES AND METHODS" filed May 17, 2002, application Ser. No. 10/150,547, (collectively referred to as "Applications for Anchored Devices") which are owned by the Assignee, and which are incorporated herein by reference. The Applications for Anchored Devices generally disclose and describe the structure, operation, placement, and removal of anchored intra-bronchial devices, such as intra-bronchial device 200.

The structure of anchored intra-bronchial device 200 includes support structure 201 and a control member 290. Support structure 201 includes a central support structure 209, an anchor base 261, and optionally control member support members 202, 203, 204, 205, 206 and 208. The anchor base 261 includes an anchor base aperture 265, anchor base angle 263, and anchors 212, 214, and 216, which include anchor ends 222, 224, and 226, and stops 252, 254, and 256, respectively. Central support structure 209 extends both proximal and distal of control member 290, and carries anchor base 261 proximal of control member 290. Central support structure 209 also distally carries the cavity 110 that is arranged for carrying the therapeutic agent 105. The linear plane of anchors 212, 214, and 216 intersect anchor base 261 at anchor base angle 263. Anchor base angle 263 is selected to optimize anchor deployment force and anchor releaseability. Stops 252, 254, and 256 include a flat area to limit the piercing of the air passageway wall by anchor ends 222, 224, and 226. In alternative embodiments, the stops can be any configuration or shape known to those skilled in the art to limit the piercing.

The anchors 212, 214, and 216 are arranged to be collapsible into a configuration for being fed through the conduit 70 in a collapsed state, and to move to an anchoring configuration upon deployment in the air passageway 50 for engaging the interior wall of the air passageway 50. The anchors are further arranged to be releaseable from the interior wall of the air passageway by engaging the intra-bronchial device 200 with an instrument, and drawing device 200 into the conduit 70 and removing it from the patient. The Applications for Anchored Devices provide additional descriptions of anchored structures, of anchoring an intra-bronchial device in an air passageway, and of releasing the anchors and removing the intra-bronchial device from an air passageway.

Flow control member 290 is similar to flow control member 90. Flow control member 290 may be formed of a flexible membrane or a solid material, is generally impervious to airflow, and may be formed of a silicone or polyurethane, for example. Flow control member 290 may have any shape suitable for accomplishing its purpose, and optimally is collapsible to enable it to be fed through the conduit 70 in a collapsed state. Control member 290 may either be supported by its own structure, or may be carried on and supported by control member support members, such as members 202, 203, 204, 205, 206 and 208. Control member 290 is arranged to be carried on the support structure 201, and to have its generally circular base orientated distally. Control member 290 is secured to the central support structure 109, and may be additionally secured to the support members at its larger diameter 91. It may be secured by adhesive, or other manner known in the art. Control member 290 may be structurally arranged, or loosely carried on support members 102, 103, 104, 105, 106, and 108, such that it expands radially outwardly when airflow is directed toward the generally circular base 94 to form a seal against the wall of the air passageway 50 and limits air and mucus flow. Control member 290 may be further structurally arranged to contract when the airflow reverses to diminish or break the seal and permit airflow. While FIGS. 15, 16a, and 16b illustrate anchoring an intra-bronchial device 200 having a flow control member 290 that is formed of a flexible membrane, in alternative embodiments, anchoring may be used with any type of intra-bronchial device that provides a therapeutic agent. Furthermore, while FIGS. 15 and 16 illustrate the anchors being carried on a support structure, in alternative embodiments the anchors may be carried on the flow control member or in any other manner associating the anchors with the intra-bronchial device. In further alternative embodiments, the anchors may be positioned distal of the control member and/or proximal of the control member.

Control member 290 may include a separator or filtration element, or semi-permeable membrane, arranged to allow movement of air and water vapor molecules, but to inhibit movement of larger molecules and mucociliary transport. For example, a separator element such as a NUCLEPORE® polycarbonate track etch membrane, a registered trademark of Whatman, Inc., of Newton, Mass., could be used for all or a portion of the control member 290. The molecules of the therapeutic agent 105 are associated with molecules larger than air and water molecules, and the separator is arranged to inhibit movement of the larger associated molecules while allowing movement of the smaller air and water vapor molecules.

Figure 17:
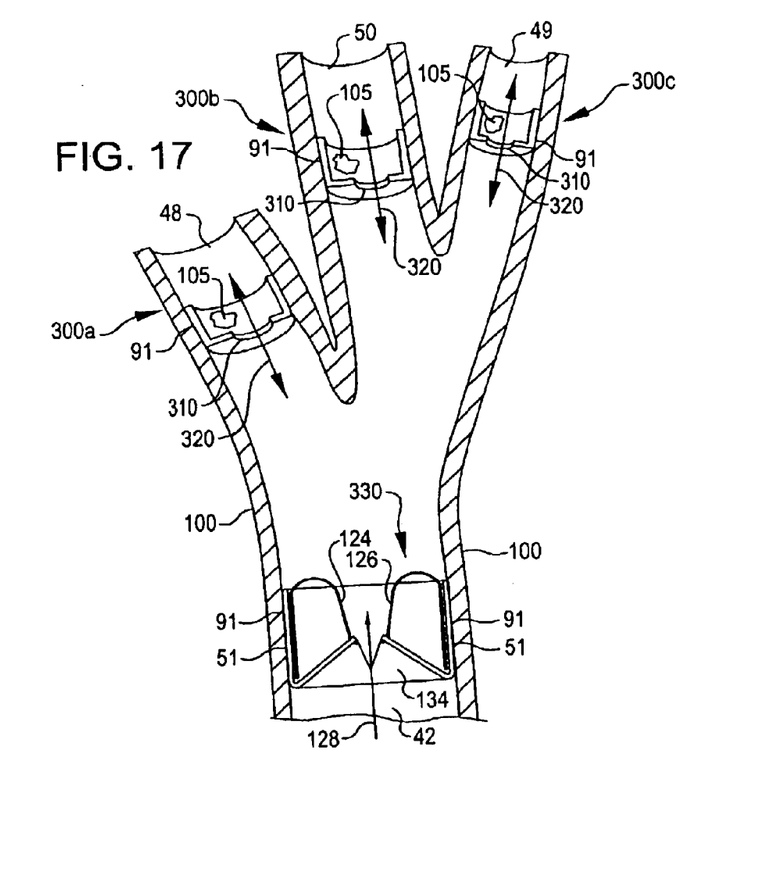
FIG. 17 illustrates an assembly of a plurality of intra-bronchial devices for providing a therapeutic agent and a flow control member for inhibiting movement of the therapeutic agent proximally, all placed in an air passageway branch, in accordance with the invention.

FIG. 17 illustrates an assembly of a plurality of intra-bronchial devices 300a–c for providing a therapeutic agent 105 and a flow control member 330 for inhibiting movement of the therapeutic agent 105 proximally, all placed in an air passageway branch, in accordance with the invention. Intra-bronchial device 330 is substantially similar in construction, placement, and operation to intra-bronchial device 120 except that it does not carry a therapeutic agent 105. Intra-bronchial device 300a–c is similar in construction, placement, and operation to intra-bronchial device 120 except the one-way valve structure is omitted. Free passage of air and moisture is permitted past intra-bronchial devices 300 through aperture 310 as depicted by arrow 320. An alternative embodiment of the intra-bronchial devices 300 and 330 may provide for mucociliary transport.

Use of multiple cooperating intra-bronchial devices as illustrated in FIG. 17 may be advantageous in treating and diagnosing certain diseases and conditions, or in certain patients, or when using certain types of intra-bronchial devices. For example, a plurality of intra-bronchial devices may be required or used to provide proper dosing of therapeutic agent 105 to a lung portion. Intra-bronchial devices that do not provide flow control may be more simple to install, may be less expensive to manufacture, and may typically have a smaller outer periphery 91 diameter in a range of 2–3 mm. In addition, the targeted bronchial branches may be too small for placement of an intra-bronchial device that provides flow control, which is presently in the range of 3–5 mm. A plurality of miniature intra-bronchial devices 300 carrying therapeutic agent 105 may be driven distal into the bronchial tree and lung tissue to treat localized disease, down to possibly 2 mm in diameter, or possibly into the bronchioli once smaller devices are developed Such miniature intra-bronchial devices 300 may be guided by very small diameter bronchoscopes, or other types of high resolution imaging techniques that may include using ancillary catheters and possibly a guidewire. For example, miniature devices could be used to treat a localized fungus disease close to the surface of the lungs, or as a method to place chemotherapy for lung cancer. The therapeutic agent 105 may be localized and confined to the lung portion by an intra-bronchial device 330 placed in a larger air passageway, such as air passageway 42.

Intra-bronchial device 300 may be any member that does not significantly obstruct flow of air. For example, the intra-bronchial device carrying therapeutic agent 105 may be a tubular member coated with therapeutic agent 105, which may be balloon expandable as is known in the art, or may be self-expanding.

Additional intra-bronchial devices and methods for providing a therapeutic agent to a patient are disclosed and claimed in INTRA-BRONCHIAL AIRFLOW CONTROL DEVICE THAT CONTROLS BIOLOGICAL INTERACTION WITH THE PATIENT filed Feb. 21, 2002, application Ser. No. 10/081,712; and INTRA-BRONCHIAL AIRFLOW CONTROL DEVICE THAT CONTROLS BIOLOGICAL INTERACTION WITH THE PATIENT filed Jun. 21, 2002, application Ser. No. 10/178,073, which are incorporated herein by reference.

While particular embodiments of the present invention have been shown and described, modifications may be made, and it is therefore intended in the appended claims to cover all such changes and modifications that fall within the true spirit and scope of the invention.

What is claimed is:

1. An intra-bronchial device comprising:
   a member configured to be implanted in an air passageway of a lung;
   a therapeutic agent overlying, embedded in, absorbed in, co-mixed with, or combinations thereof, at least a portion of the member and arranged for provision to a patient; and
   at least one anchor that retains the intra-bronchial device within the air passageway when the anchor is deployed.

2. The intra-bronchial device of claim 1, wherein the member is further arranged for inhibiting the therapeutic agent from moving proximal of the member.

3. The intra-bronchialdevice of claim 1, wherein said member has a generally conical configuration with a base portion, said base portion being generally circular and having a periphery for contacting the walls of the air passageway.

4. The intra-bronchial device of claim 3, wherein at least one anchor is releasable from the air passageway for removal of the intra-bronchial device.

5. The intra-bronchialdevice of claim 1, wherein the member comprises means for limiting air flow and/or mucociliary transport when said device is implanted in said air passageway.

6. The intra-bronchial device of claim 1, wherein the member comprises a one-way valve configured to allow fluid flow in one direction and to prohibit fluid flow in an opposite direction.

7. The intra-bronchial device of claim 1, wherein the member comprises a flexible membrane impervious to air flow.

8. The intra-bronchial device of claim 1, wherein the membrane is supported by a metallic frame.

9. The intra-bronchial device of claim 1, wherein the member comprises a semi-permeable membrane configured to prevent the therapeutic agent from passing therethrough while permitting air and water molecules to pass therethrough.

10. The intra-bronchial device of claim 1, wherein the member further comprises an absorptive portion and the therapeutic agent is absorbed by said absorptive portion.

11. The intra-bronchial device of claim 1, wherein said member comprises a cavity, and the therapeutic agent is carried in the cavity.

12. The intra-bronchial device of claim 11, wherein the cavity includes a cover having an orifice.

13. The intra-bronchial device of claim 2, wherein said member has a generally conical configuration with a base portion, said base portion being generally circular and having a periphery for contacting the walls of the air passageway.

14. The intra-bronchial device of claim 1, wherein said member has a generally cylindrical configuration formed by a sidewall configured to contact the walls of the air passageway.

15. The intra-bronchial device of claim 1, wherein said member is secured to a central support structure, and said member is supported by support members attached to said support structure.

16. The intra-bronchial device of claim 1, wherein the therapeutic agent comprises at least one of an antimicrobial agent, antibiotic agent or antibacterial agent, antiviral agent, anthelmintic agent, anti-inflammatory agent, antineoplastic agent, antioxidant agent, biological reaction inhibitor, botulinum toxin agent, chemotherapy agent, diagnostic agent, gene therapy agent, hormonal agent, mucolytic agent, radioprotective agent, radioactive agent, tissue growth inhibitor, tissue growth enhancer, and vasoactive agent.

* * * * *

UNITED STATES PATENT AND TRADEMARK OFFICE
CERTIFICATE OF CORRECTION

| | | |
|---|---|---|
| PATENT NO. | : 6,929,637 B2 | Page 1 of 1 |
| APPLICATION NO. | : 10/317667 | |
| DATED | : August 16, 2005 | |
| INVENTOR(S) | : Hugo X. Gonzalez et al. | |

It is certified that error appears in the above-identified patent and that said Letters Patent is hereby corrected as shown below:

On the Title Page, Item (56)

After "4,086,665  A  5/1978  Poirier" insert -- 5,314,473  A  5/1994  Godin, Norman J. --

After "5,314,473  A  5/1994  Godin, Norman J." insert -- 5,803,078  A  9/1998  Brauner, Mark E. --

After "5,803,078  A  9/1998  Brauner, Mark E." insert -- 6,242,472  A  6/2001  Sekins et al. --

After "6,242,472  A  6/2001  Sekins et al." insert -- 6,558,429  A  5/2003  Taylor, Thomas V. --

Title Page 2, Item (56) 2nd col. Line 47, Delete "Buch et al." and insert -- Soltesz et al. --

Signed and Sealed this
Eighth Day of February, 2011

David J. Kappos
*Director of the United States Patent and Trademark Office*